(12) United States Patent
Bosanac et al.

(10) Patent No.: US 12,191,040 B2
(45) Date of Patent: Jan. 7, 2025

(54) ASSESSING DISEASE RISKS FROM USER CAPTURED IMAGES

(71) Applicant: Advanced Human Intelligence Ltd., South Perth (AU)

(72) Inventors: Vlado Bosanac, South Perth (AU); Amar El-Sallam, South Perth (AU)

(73) Assignee: Advanced Health Intelligence Ltd., South Perth (AU)

( * ) Notice: Subject to any disclaimer, the term of this patent is extended or adjusted under 35 U.S.C. 154(b) by 367 days.

(21) Appl. No.: 17/695,627

(22) Filed: Mar. 15, 2022

(65) Prior Publication Data

US 2022/0301723 A1  Sep. 22, 2022

Related U.S. Application Data

(60) Provisional application No. 63/161,881, filed on Mar. 16, 2021.

(51) Int. Cl.
*G16H 50/30* (2018.01)
*A61B 5/00* (2006.01)
*A61B 5/021* (2006.01)
*A61B 5/024* (2006.01)
*A61B 5/026* (2006.01)
(Continued)

(52) U.S. Cl.
CPC ............ *G16H 50/30* (2018.01); *A61B 5/026* (2013.01); *G06N 20/00* (2019.01); *G06V 40/10* (2022.01); *G16H 30/40* (2018.01); *G16H 50/20* (2018.01)

(58) Field of Classification Search
None
See application file for complete search history.

(56) References Cited

U.S. PATENT DOCUMENTS

2009/0082637 A1  3/2009 Galperin
2015/0317446 A1  11/2015 Ash et al.
(Continued)

FOREIGN PATENT DOCUMENTS

WO  WO-2018190403 A1 * 10/2018  ............. A61B 5/004
WO  WO-2020056196 A1 *  3/2020  ............ G06T 7/0012
WO  WO-2020132713 A1 *  7/2020  ............ A61B 5/0013

OTHER PUBLICATIONS

International Search Report and Written Opinion of International Application No. PCT/AU2022/050226, mailed May 20, 2022.
(Continued)

*Primary Examiner* — Mohammed Rachedine
(74) *Attorney, Agent, or Firm* — Dorsey & Whitney LLP

(57) ABSTRACT

In some examples, an apparatus, such as a mobile phone can include an input module such as a touch screen, a camera, a processor, and computer readable medium. The camera captures one or more images of a person. The processor can use a single machine learning model to estimate the human body features of the person based on the captured images, and use the human body features to generate a disease risk assessment value associated with diabetes and cardiovascular disease risks. The human body features can include at least one or more of: 3D body shape, or body shape indicators; and one or more of: blood flow, blood pressure, heart rate, respiratory rate, heart rate variability, cardiac workload, irregular heartbeats, or stress index. The machine learning model can be trained over a set of training images.

20 Claims, 5 Drawing Sheets

(51) Int. Cl.
*A61B 5/08* (2006.01)
*G06N 20/00* (2019.01)
*G06V 40/10* (2022.01)
*G16H 30/40* (2018.01)
*G16H 50/20* (2018.01)

(56) References Cited

U.S. PATENT DOCUMENTS

| | | | |
|---|---|---|---|
| 2016/0055758 A1 | 2/2016 | Francis | |
| 2016/0247017 A1* | 8/2016 | Sareen | A61B 5/7475 |
| 2017/0300655 A1* | 10/2017 | Lane | G16H 10/60 |
| 2021/0133276 A1* | 5/2021 | Dolan | G06Q 10/067 |
| 2022/0044817 A1* | 2/2022 | Watanabe | G16H 50/20 |

OTHER PUBLICATIONS

Heuberger, R., et al., "Body scanning as a new anthropometric measurement tool for health-risk assessment", International Journal of Consumer Studies, 32: 34-40. DOI:10.1111/j.1470-6431.2007. 00626.x [retrieved from internet May 19, 2022].

Ng, B., et al., "Detailed 3-dimensional body shape features predict body composition, blood metabolites, and functional strength: the Shape up! studies", American Journal of Clinical Nutrition. Dec. 1, 2019;110(6):1316-1326. doi: 10.1093/ajcn/nqz218. [retrieved from internet May 19, 2022] <URL: https://academic.oup.com/ajcn/article/110/6/1316/5573708> [published Sep. 25, 2019].

* cited by examiner

ASSESSING DISEASE RISKS FROM USER CAPTURED IMAGES

FIELD

The described embodiments relate generally to machine learning systems, and specifically relate to increasing the accuracy of machine learning systems by combining multiple predictive techniques.

BACKGROUND

Despite advancements in health care and modern medicine, accurate detection of chronic diseases, such as cardiovascular disease, obesity, and type-2 diabetes, continue to be a challenge. Millions of lives can be saved, and quality of life improved, through early detection. However, the detection of these chronic diseases still suffer due to the need for traditionally expensive and inaccessible medical equipment, such as scanners and blood pressure monitors, and the inaccuracy of many traditional techniques that mainly rely on basic human body measurements, such as body mass index (BMI) calculation, which is largely based on a person's weight, height, age, or other information.

Various statistical methods using body measurements are done with regression models and limited degrees of freedom. Some traditional machine learning systems with higher degrees of freedom have also been explored. However, traditional machine learning systems can be limited based on inherent design inaccuracies, statistical outliers, and/or relatively small data-sets and experience. Therefore, it may be desirable to assess a person's chronic disease risks inexpensively, safely, and accurately, using additional human data and data sensory.

SUMMARY

One aspect of the present disclosure relates to an apparatus including an input module configured to retrieve first input data and second input data, a processor, and computer readable medium containing programming instructions. When executed, the programming instructions will cause the processor to create a 3D body shape model from the first input data and the second input data, the 3D body shape model including biometrics, use the biometrics to generate health risk indicators and assessments including a first disease risk assessment value, generate a second risk assessment value based on the second input data, and fuse the biometrics with the first and second input data, and optionally the first disease risk assessment value and the second disease risk assessment value to generate a multi-category disease risk assessment value.

In one example, the input data module is integrates with an image capturing device configured to capture one or more images of a subject. In one example, the second input data include the one or more images of the subject. In one example, the diabetes risk assessment value is based on the one or more images.

In one example, the first disease includes diabetes. In one example, the second disease includes cardiovascular disease.

One aspect of the present disclosure relates to an apparatus including an image capturing device configured to capture one or more images of a subject, a processor, and a computer readable medium. The computer readable medium contains programming instructions that, when executed, will cause the processor to use a 3D body shape model to generate a diabetes risk assessment value based on the one or more images, generate a cardiovascular risk assessment value based on the one or more images, and fuse the diabetes risk assessment value and the cardiovascular risk assessment value to generate a disease risk assessment value.

According to some examples, the programming instructions are further configured to update the 3D body shape model based on an output of the fusion of the diabetes risk assessment value and the cardiovascular risk assessment value.

In some examples the programming instructions are further configured to use the 3D body shape model to generate first biomarkers from the one or more images, the first biomarkers representing body features, and generate the diabetes risk assessment value based on the body features. In some examples, the first biomarkers include one or more of: 3D body shapes or body shape indicators. According to one example, the diabetes risk assessment value can indicate a risk associated with one or more of: type-2 diabetes, obesity, central obesity, or metabolic syndrome.

According to one example, the programming instructions can be further configured to generate second biomarkers from the one or more images, the second biomarkers representing heart disease related biomarkers, and generate the cardiovascular assessment value based on the second biomarkers. The second biomarkers can include one or more of: blood flow, blood pressure, heart rate, respiratory rate, heart rate variability, cardiac workload, irregular heartbeats, or stress index. According to one example, the cardiovascular risk assessment value can indicate a risk associated with one or more of: cardiovascular disease, heart attack, or stroke.

In one example, the programming instructions can be further configured to generate the second biomarkers from facial images of the one or more images, wherein the second biomarkers include at least blood flow.

In another aspect of the present disclosure, an apparatus can include an input data configured to retrieve input data, a processor, and a computer readable medium. The computer readable medium can contain programming instructions that, when executed, will cause the processor to use a disease risk model to generate human body feature from the input data, and generate a disease risk assessment value based on the human body feature. According to one example, the human body feature includes at least one or more of: 3D body shape, or body shape indicators; and one or more of: blood flow, blood pressure, heart rate, respiratory rate, heart rate variability, cardiac workload, irregular heartbeats, or stress index.

In one example, the disease risk assessment value indicates a risk associated with at least: one or more of: type-2 diabetes, obesity, central obesity, or metabolic syndrome; and one or more of: cardiovascular disease, heart attack, or stroke.

In one example, the programming instructions can be further configured to generate the disease risk model from one or more training images using a machine learning network.

In one example, the input data module can include an image capture device configured to capture one or more images of the subject. In one example, the input data can include the one or more images of the subject.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Certain details are set forth below to provide a sufficient understanding of examples of various embodiments of the disclosure. However, it is appreciated that examples described herein may be practiced without these particular details. Moreover, the particular examples of the present disclosure described herein should not be construed to limit the scope of the disclosure to these particular examples. In other instances, well-known circuits, control signals, timing protocols, and software operations have not been shown in detail in order to avoid unnecessarily obscuring embodiments of the disclosure. Additionally, terms such as "couples" and "coupled" mean that two components may be directly or indirectly electrically coupled. Indirectly coupled may imply that two components are coupled through one or more intermediate components.

Systems and methods described herein can be configured to receive input data, including images, to infer a 3D body model generated using artificial intelligence (AI) and machine learning models. These models can then be used to generate health risk and assessment indicators, for example a cardiovascular risk assessment value or a diabetes risk indicator based on the one or more of the input data and images. In addition, systems and methods described herein can be configured to fuse or combine the various risk assessment values to generate more accurate and broader multivariate-driven disease and health risk assessment values.

Figure 1:
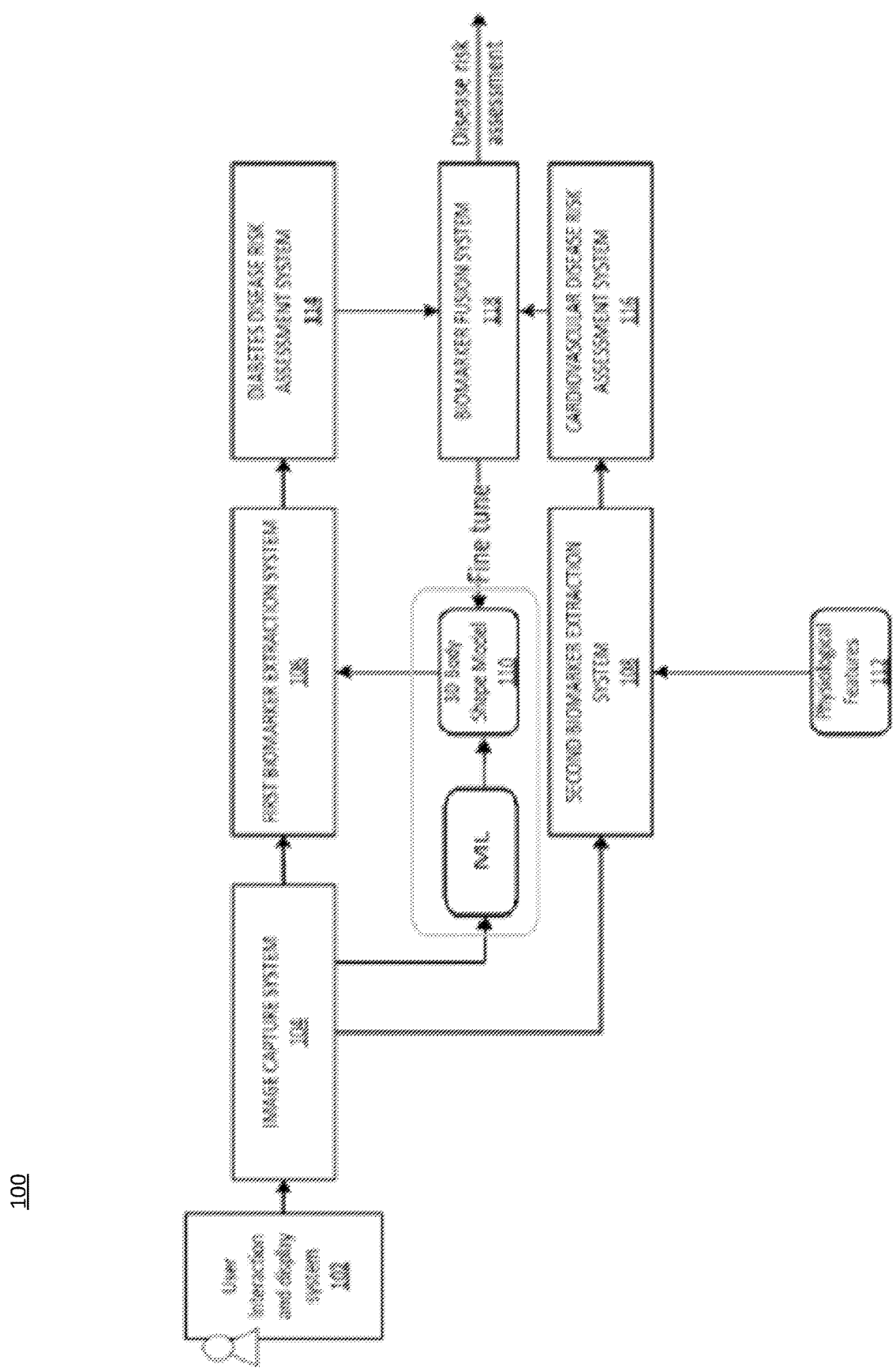
FIG. 1 is a block diagram of a system for assessing a person's disease risks according to some examples described in the disclosure.

FIG. 1 is a block diagram of a system for assessing a person's disease risks according to some examples described in the disclosure. In some examples, a disease risk assessment system 100 can include a input data module with an image capture system 104, for example an input data module including an image capturing device, configured to capture one or more user images and additional human data. The image capture system can include an image capture device, such as a camera (e.g., a mobile phone or another hand-held computing device with built-in camera or a stationary camera). The data input module including the image capture device can be configured to capture one or more photographic images of a user in multiple views. The human data can be age, weight, ethnicity, or other historical health data.

In some examples, the system 100 can include a user interaction and display system 102 coupled to the input data module, including coupled to the image capture system 104. The user interaction and display system 102 can include a computer display configured to provide visual and audio aids to guide the user to capture optimal images depending on whether the user is capturing the images by herself/himself, or another person is capturing the images. For example, during the capturing of user images, the user interaction and display system 102 can display a visual representation of a human body, such as skeleton, a generic body silhouette, a target including a number of alignment features, or other indicators configured to guide the user to move a part of the body to a desired position so that the captured body image aligns with the visual representation.

In some examples, the visual representation can include a human body contour, a bounding box or bars, or other symbols to indicate a suggested position of one or more body parts or a whole body of the user. As used herein, the term "skeleton" should be interpreted broadly to include body contours, bounding boxes (or other geometries), linear skeleton representations including joints, independent targets representing body and/or joint locations, and the like. Additionally, any number or combinations of the visual representations or skeletons can be used. For example, the system 102 can display a visual representation in the form of a skeleton of arms to guide the user to move the arms or stretch the arms in a desired posture. Similarly, the system 102 can display a skeleton or a body structure or other visual representation of an entire body, which can include the head, the arms, the legs, the chest, and/or other parts of the body. The skeleton or the contour or the joints can be generated based on a first data input by the input data module, including a captured user image from the image capturing device of the image capture system, such that the skeleton or the contour or generally the guiding aid is displayed on the display of the user interaction and display system 102 in proportion to the images being captured. The guiding aid is displayed to guide the user to capture a second or more of the user images subsequent to the first captured user image. In some examples, the user interaction and display system 102 can be stand alone and external to the image capture system 104. In other scenarios, the user interaction and display system 102 can be integrated with the image capture system 104, for example, in a mobile phone.

In some examples, the system 100 can include a first biomarker extraction system, which can be configured to extract first biomarkers based on the captured user images from the image capture system 104. Examples of the first biomarkers can include a 3D body shape. The first biomarkers can also include body shape indicators in some embodiments. Examples of body shape indicators can include body volume, body fat, bone mineral density or other indicators. The first biomarker can be extracted based on a 3D body shape model 110. The 3D body shape model can include a 3D representation of a human body. The 3D body shape model can also include body shape indicators, such as body volume, body fat, bone mineral density, etc. In a non-limiting example, 3D body shape indicators can include total body fat, waist-to-height ratio, waist-to-hip ratio, waist circumference, chest circumference, hips circumference, and circumference of the subject's thighs.

The 3D body shape model can be trained from user images, in that the 3D body shape model represents the relationship between user images and 3D body shape and body shape indicators. For example, the 3D body shape model can be trained by a 3D representation system. The 3D representation system can also be configured to receive user images captured from the image capture system 104 and use the 3D body shape model to estimate the 3D body shape and body shape indicators of a human body based on the user images. In some examples, the 3D body shape model can include a collection of 3D body shape models, each representing an individual or a group of people.

With further reference to FIG. 1, in some examples, the 3D body shape model can also be trained based on body scan parameters in a body scan database 124. In some examples, the body scan parameters can be collected from DEXA scans for various parts of a human body. For example, the body scan parameters can include body fat and/or bone mineral density (measured in Z-score and T-score) for different parts of a body, such as the torso, the thigh, or the waist etc. In some examples, the 3D body shape model can be trained in a machine learning network. The details of 3D body shape and composition model training will be further described in the present disclosure, with reference to FIGS. 2 and 4.

In some examples, the system 100 can include a diabetes disease risk assessment system 114, which is configured to receive the first biomarkers from the first biomarker extraction system 106, such as the estimated 3D body shape and body shape indicators. The diabetes disease risk assessment system 114 can use the estimated first biomarkers to generate diabetes disease risk values. Diabetes disease risk values can include multiple values representing the risk of diabetes, such as Type-2 diabetes risk, obesity risk, central obesity risk, and metabolic syndrome risk. In some examples, the diabetes disease risk values can be obtained based on the first biomarkers such as 3D body shape and body shape indicators. Additionally, the diabetes disease risk values can be obtained based on a change of one or more of the first biomarkers over time. For example, the system can determine the change of body fat, and/or other body shape indicators, over a period of time, and based on the change of these indicators over time, determine an obesity risk value.

With continued reference to FIG. 1, the system 100 can further include a second biomarker extraction system 108, which can be configured to extract second biomarkers based on the captured images from the image capture system 104. Examples of the second biomarkers can include heart disease related biomarkers, such as blood pressure, heart rate, respiratory rate. The examples of second biomarkers can also include heart rate variability, cardiac workload, irregular heartbeats, and stress index. In some examples, the second biomarkers can be obtained from physiological features 112.

With further reference to FIG. 1, the physiological features can be obtained from health sensors or health data. For example, a patient can take a blood pressure test on a daily basis, and health data such as blood pressure, heart rate, and respiratory rate can be obtained. In some examples, one or more of the biomarkers can be detected from user images captured from the image capture system 104. Whereas human skin is translucent, light and its respective wavelengths can be reflected at different lengths below the skin and reveal blood flow information. This makes it possible to detect blood flow from one or more camera images. Similar to a facial scan, the image capture system 104 can be configured to capture a thumb images/video, or the face images/video or extracted data from a smart sensor such as a smart watch of a user, and detect the blood flow from the captured face images. According to one embodiment, the captured face images can be videos and/or still images.

In some examples, the user interaction and display system 102 can be configured to guide the user during the capturing/detecting of the blood flow. For example, the user interaction and display system 102 can provide a user interface on a display to guide the user to stand still while the image capture system is determining the blood flow from a sequence of facial images. In some examples, the blood flow, and/or other second biomarkers can be detected from images of other parts of the human body, such as the entire face or specific portions of the face, such as the nose, eyes, ears, cheeks, forehead, lips, etc. Additionally, other portions of the body can be used to provide indicators, such as hands, wrists, feet, etc.

In some examples, the system 100 can include a cardiovascular disease risk assessment system 116, which is configured to receive the second biomarkers from the second biomarker extraction system 108, such as blood pressure, heart rate, respiratory rate, heart rate variability, cardiac workload, irregular heartbeats, and stress index. Based on these biomarkers, the system can determine the risk assessment associated with heart diseases, such as cardiovascular disease risk, heart attack risk, and stroke risk. In some examples, the risk assessment can be represented in one or more assessment values, such as cardiovascular risk value, heart attack risk value etc.

With further reference to FIG. 1, the system 100 can include a biomarker fusion system 118, configured to fuse the diabetes risk assessment and the cardiovascular risk assessment obtained from the diabetes disease risk assessment system 114 and cardiovascular disease risk assessment system 116, respectively. For example, the biomarker fusion system 118 can compare a diabetes risk assessment value with a heart attack risk value and determine if there is any inconsistency between the two assessment values. Based on the comparison, the fusion system 118 can adjust the diabetes risk assessment value or the heart attack risk value. This results in more accurate disease risk assessment than the diabetes disease risk assessment system or cardiovascular disease risk assessment system alone provides. For example, convergence of the two assessment values is indicative of an accurate assessment, and the confidence level of the risk assessment value can be increased due to the validation and similarity between the two assessment values. Similarly, if the two assessment values diverge or are inconsistent with one another, additional measurements can be taken, or the outliers can be disregarded. In some examples, the two assessment values are independently determined and their combinations can be evaluated for an overall or combined risk assessment, the varying values being indicative of different potential results.

In some examples, the result of the fusion system 118 can be used to fine-tune the 3D body shape model 110. For example, if it is determined from the fusion system 118 that the diabetes disease risk assessment value needs to be adjusted, the one or more biometric indicators of the 3D body shape model that contributed to the diabetes risk can also be adjusted. In some examples, if the 3D body shape model is learned from a machine learning network, the machine learning network can also be tuned based on the result of the biomarker fusion system 118. The fine-tuned 3D body shape model then will be used in future operations of the first biomarker extraction system 106. Alternatively, and/or additionally, the first biomarker extraction system 106 can be configured to re-run after the 3D body shape model 110 is adjusted.

Figure 2:
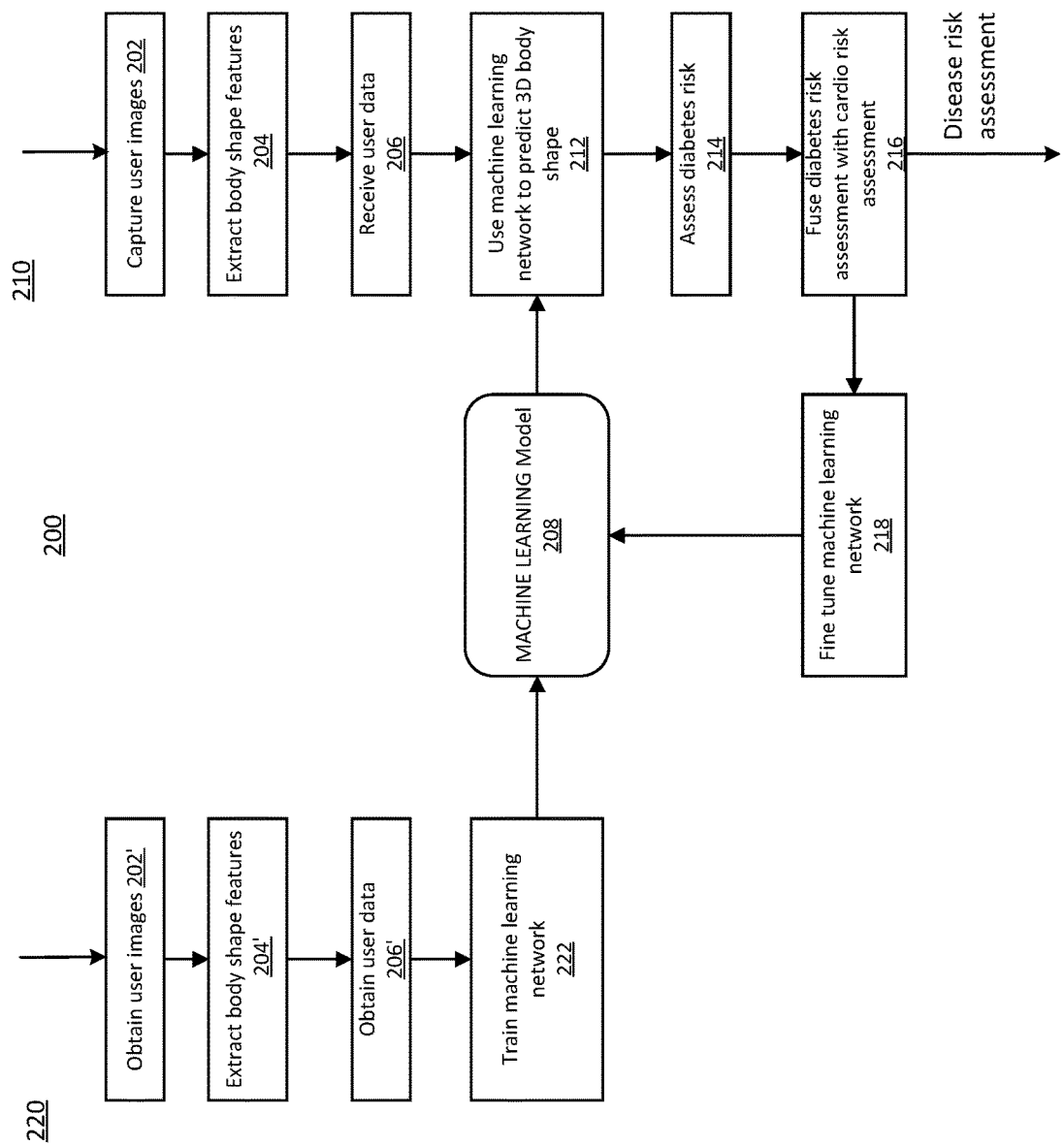
FIG. 2 is an example process for assessing a person's disease risks using a machine learning network according to some examples described in the disclosure.

FIG. 2 is an example process for assessing a person's disease risks using a machine learning network, according to some examples described in the disclosure. In some examples, the example process 200 can be implemented in disease risk assessment system 100 in FIG. 1. With reference to FIG. 2, the process 200 can include a prediction process 210. The prediction process 210 can include capturing user images at operation 202. For example, the operation 202 can be performed in the image capture system 104 (FIG. 1) to obtain one or more user images, such as a front image, side image, back image, and/or user images from different angle. The user images can be facial images, upper body images, and/or whole body images.

In some examples, the process 210 can further include extracting body shape features at operation 204. In some examples, the operation 204 can be implemented in the first biomarker extraction system 106 (FIG. 1). Examples of the body shape features can include 2D silhouettes representing the foreground of a human body, 2D joints or other body shape features. In some examples, the body shape features can be obtained based on the captured user images. Additionally, and/or alternatively, the process 210 can further include receiving user data at operation 206. For example, the operation 206 can receive user entered data, e.g., user's weight, height, age, gender, ethnic group etc. This operation can be implemented in the user interaction and display system 102 (FIG. 1), in some examples. Operation 206 can further assess one or more databases to retrieve other user data, such as user health fitness data.

With further reference to FIG. 2, the process 210 can further include using a machine learning network to predict 3D body shape at operation 212, based on the extracted body shape features (204) and/or received user data (206). Operation 212 can be implemented in the first biomarker extraction system 106 (FIG. 1), in some examples. As discussed with respect to embodiments in FIG. 1, the predicted 3D body shape can include first biomarkers, such as 3D body shape and body shape indicators (e.g., body volume, body fat, bone mineral density or other indicators). Similar to FIG. 1, the first biomarkers can be obtained using a machine learning model 208. The machine learning model can include a 3D body shape model, such as 110 (in FIG. 1).

With further reference to FIG. 2, process 210 can further include assessing diabetes risk at operation 214. In some embodiments, the operation 214 can be implemented in the diabetes disease risk assessment system 114 (FIG. 1), to generate diabetes disease risk assessment values. Process 210 can further include fusing the diabetes risk assessment and cardiovascular risk assessment at operation 216. In some examples, the diabetes risk assessment can be obtained from the diabetes disease risk assessment system 114 (FIG. 1). The cardiovascular risk assessment can be obtained from the cardiovascular disease risk assessment system 116 (FIG. 1). The operation 216 can be implemented in the biomarker fusion system 118 (FIG. 1), to generate disease risk assessment. In some examples, the process 210 can further include fine tuning the machine learning network at operation 218, based on the output of the fusion operation 216.

Now, with further reference to FIG. 2, the process 200 can further include a training process 220 for training the machine learning model 208. In some examples, the process 220 can include obtaining the user images at operation 202', extracting body shape features at operation 204', and obtaining user data at operation 206'. The process 220 can use the images/features/data from the operations 202', 204', and/or 206', to train the machine learning model at operation 222. The processes 202', 204', and 206' can be performed in the same manner as processes 202, 204 and 206, respectively, except that the user images obtained from operation 202' are different from the user images captured from operation 202, and that the user data obtained from 206' are different from those obtained from 206.

In non-limiting examples, the operation 202' can retrieve user images from a training data set. For example, the training data set can contain a collection of training user images and/or training user data previously captured or collected, along with ground truth data associated with the training data set. The ground truth data can contain the ground truth 3D body shape and/or other body features.

In some examples, the training data can include multiple sets each collected from a subject in a group of subjects, and each set containing a corresponding ground truth data. In some examples, the operation 222 can train the machine learning network to generate a machine learning model 208 based on the collected training data. In some examples, the training process 222 can generate a single machine learning model 208 based on the collected training data from the group of subjects. The collected data can be used to modify the weights and parameters for the machine learning model.

In some other examples, the training process 222 can generate multiple machine learning models 208, each based on the training data from a sub-group of subjects or a single subject. For example, the training process can generate a machine learning model for a sub-group of the graining subjects divided by ethnic group, by gender, by age, by height, or by other demographical measures, such as profession, education etc. The machine learning model 208 can thus include one or more 3D body shape models (e.g., 110 in FIG. 1).

Returning to process 210, the user images and user data (e.g., weight, height, age, etc.) can be obtained in real-time from the user via the image capture system 104 and/or user interaction and display system 102. The user data can also be obtained from one or more sensors or databases (e.g., user fitness data) as previously described. The operation of assessing the disease risk can be performed using the machine learning model 208 learned from the process 220. An output from the fusion operation can be used in operation 218 to fine tune the machine learning model 208.

Figure 3:
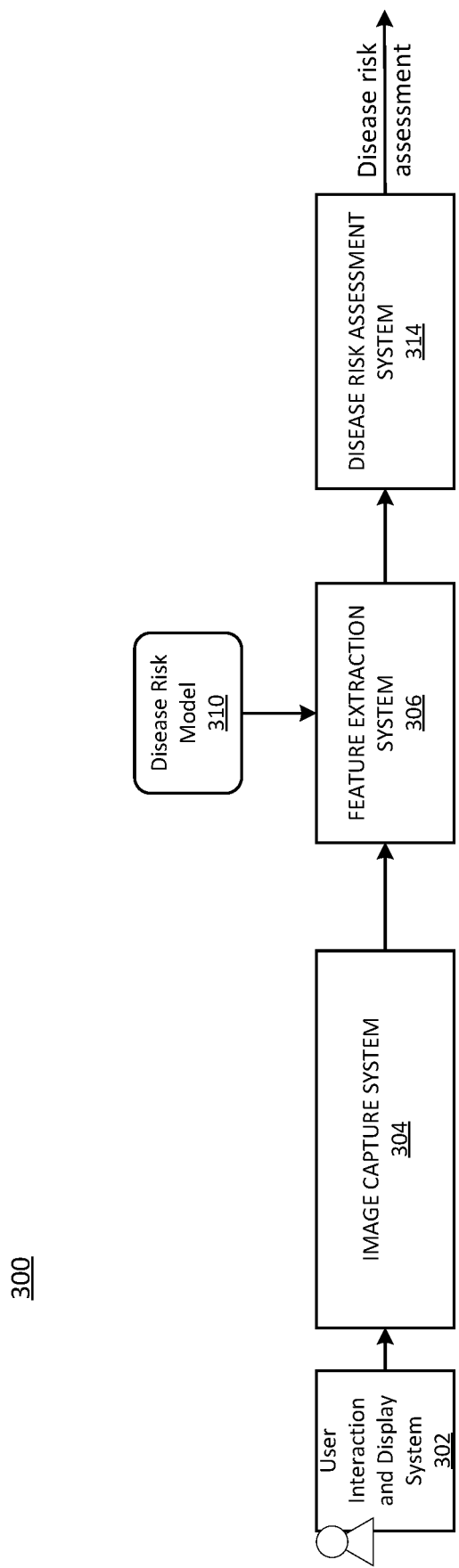
FIG. 3 is a block diagram of a system for assessing a person's disease risks according to some examples described in the disclosure.

FIG. 3 is a block diagram of a system for assessing a person's disease risks according to some examples described in the disclosure. A disease risk assessment system 300 can include one or more components similar to those in the system 100 (FIG. 1). For example, the user interaction and display system 302 and image capture system 304 can be similar to the user interaction and display system 102 and image capture system 104, the description of which will not be repeated. In some examples, the system 100 can include a feature extraction system 306 configured to extract human body features from the captured images from the image capture system 304. Examples of the human body features can include 3D body shape and body shape indicators (e.g., first biomarkers) previously described in the embodiments of FIG. 1. The human body features can also include heart disease related biomarkers, such as those corresponding to the second biomarkers described in the embodiments in FIG. 1. In other words, the feature extraction system 306 can extract both the human body features and heart disease related biomarkers together using a single disease risk model 310.

Similar to embodiments in FIG. 1, the disease risk model 310 can be trained from user images by a machine learning network. For example, the disease risk model can be trained by a disease risk model training system. In some examples, the disease risk model can include weights and/or parameters representing the relationships between user images (and/or user data) and various 3D body shape and heart disease related features. These weights/parameters are learned from a collection of training data set. The training of the disease risk model will be further described in detail with reference to FIG. 4.

Additionally, and/or alternatively, the feature extraction system 306 can also extract physiological features directly from the user captured images. For example, some features such as blood flow, can be extracted from one or more camera images based on image processing at micro-pixel level. Similar to the embodiments in FIG. 1, the image capture system 304 can be configured to capture the face images of a user, and detect the blood flow from the captured thumb or face images or suitable body part or device such as smart watches sensors. In some examples, the user interaction and display system 302 can be configured to guide the user during the capturing/detecting of the blood flow, similar to what was described in the embodiments in 102 (FIG. 1). In some examples, the blood flow, and/or other physiological features can be detected from facial images, partial facial images, or images of other parts of the human body. The extracted physiological features can be provided to the disease risk model 310 to generate heart disease related features, as similarly described in embodiments in FIG. 1.

In some examples, the system 300 can include a disease risk assessment system 314 configured to receive the human body features from the feature extraction system 306, such as the 3D body shape, body shape indicators, and heart disease related biomarkers. The disease risk assessment system 314 can use the extracted human body features to generate one or more disease risk values. For example, the disease risk values can include multiple values representing the risk of diabetes, such as Type-2 diabetes risk, obesity risk, central obesity risk, and metabolic syndrome risk, and the risk of heart problems, such as cardiovascular disease risk, heart attack risk, and stroke risk. Assessing the disease risks can be performed in a similar manner as the diabetes disease risk assessment system (114) and cardiovascular disease risk assessment system (116) in FIG. 1, for example. The details of assessing risks associated with these diseases will not be repeated.

Figure 4:
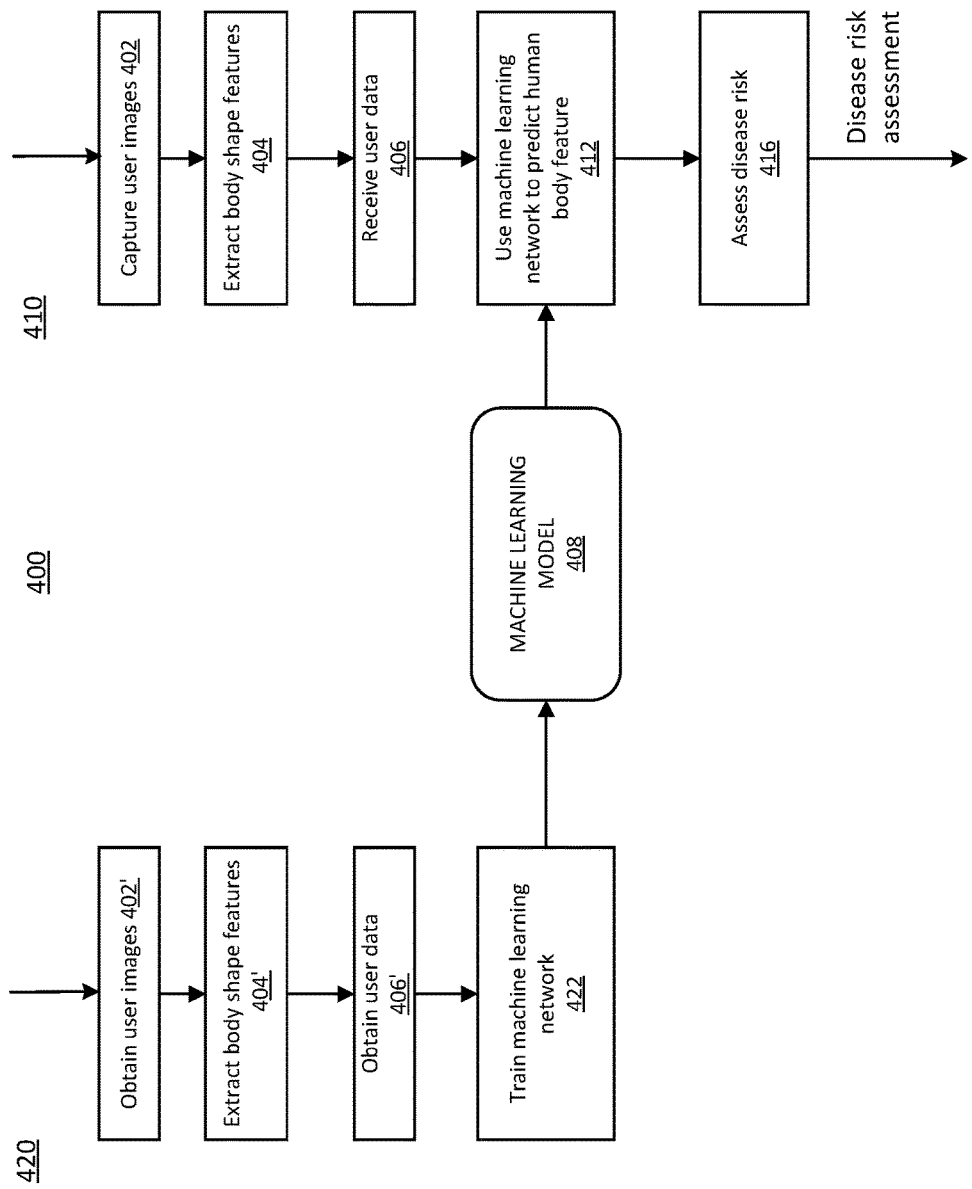
FIG. 4 is an example process for assessing a person's disease risks using a machine learning network according to some examples described in the disclosure.

FIG. 4 is an example process for assessing a person's disease risks using a machine learning network according to some examples described in the disclosure. In some examples, the example process 400 can be implemented in disease risk assessment system 300 in FIG. 1. With reference to FIG. 4, the process 400 can include a prediction process 410. The prediction process 410 can include capturing user images at operation 402, extracting body shape features at operation 404, and/or receiving user data at 406. The operations 402, 404, and 406 can be performed in a similar manner as operations 202, 204 and 206, respectively, in FIG. 2. Thus, the descriptions of those operations will not be repeated.

In comparing to operations 204, 206 in FIG. 2, the operations 404, 406 can extract or receive additional features or user data that are related to heart disease. For example, extracting body shape features 404 can additionally extract other features such as blood flow from the captured images. Receiving user data 406 can also receive additional user data related to heart disease, such as user's blood flow, heart rate, or other health data.

With continued reference to FIG. 4, the process 410 can further include using a machine learning model 408 to predict human body features at 412, based on the extracted features from operations 404, 406. Operation 412 can be implemented in the feature extraction system 306 (FIG. 3), in some examples. As discussed with respect to embodiments in FIG. 3, the predicted human body features can include 3D body shape and body shape indicators (e.g., body volume, body fat, bone mineral density or other indicators). Additionally, the human body features can include heart disease related features, such as those similar to the second biomarkers described in embodiments of FIG. 1. Thus, the machine learning model 408 can include the relationship between the training user images/user data and the various human body features.

With further reference to FIG. 4, process 410 can further include assessing health risk including diabetes risk at operation 414. The operation 414 can be implemented in the disease risk assessment system 314 (FIG. 3), in some embodiments, to generate disease risk assessment values. In some examples, the disease risk assessment can be obtained from the disease risk assessment system 314 (FIG. 3). Thus, the disease risk assessment can include risk assessment values for diabetes and cardiovascular diseases.

The process 400 can further include a training process 420 for training the machine learning model 408. In some examples, the process 420 can include obtaining the user images at operation 402', extracting body shape features at operation 404', and obtaining user data at operation 406'. The process 420 can use the images/features/data from the operations 402', 404', and/or 406', to train the machine learning model at operation 422. The processes 402', 404', and 406' can be performed in a similar manner as processes 402, 404 and 406, respectively, except that the user images obtained from operation 402' are different from the user images captured from operation 402, and that the user data obtained from 406' are different from those obtained from 406. In non-limiting examples, the operation 402' can retrieve user images from a training data set, in a similar manner as operation 202' (in FIG. 2), the description of which will not be repeated.

In some examples, the training data can include multiple sets each collected from a subject in a group of subjects, and each set containing a corresponding ground truth data. In some examples, the operation 422 can train the machine learning network based on the collected training data to generate a machine learning model 408. In some examples, the training process 422 can generate a single machine learning model 408 based on the collected training data from the group of subjects. The training process 422 can be similar to 222 (in FIG. 2), except the features used in the training are different in that the training is done for an integrated machine learning network including both diabetes and cardio features.

In some other examples, the training process 422 can generate multiple machine learning models 408, each based on the training data from a sub-group of subjects or a single subject. For example, the training process can generate a machine learning model for a sub-group of the graining subjects divided by ethnical group, by gender, by age, by height, or by other demographical measures, such as profession, education etc. The machine learning model 408 can thus include one or more disease risk models (e.g., 310 in FIG. 3). Returning to process 410, the operation of assessing the disease risk can be performed using the machine learning model 408 learned from the process 420.

Returning to systems 100 and 300 in FIGS. 1 and 3, respectively, the systems can include a training system to train and optimize one or more machine learning models based on training data. The training data can be obtained from user image database, body scan database, and/or medical image database. In some examples, the systems can be configured to train a 3D shape model of a human body. In a non-limiting example, a 3D shape model can comprise a plurality of 3D shape parameters. Examples of 3D shape parameters can include height, weight, chest circumferential measurement, or general anthropometric measurements etc., or additional parameters associates with a human body shape. In a non-limiting example, the 3D shape parameters can include 15 parameters. Other suitable number of body shape parameters can also be possible. For example, three parameters, including height, weight, and gender can be used. In one or more other examples, more than three parameters or more than 15 parameters can be possible.

In some examples, the systems can be configured to train a 2D joint model of a human body from user images, e.g., those captured from the image capture system 104. The 2-D joint model can include multiple joints of a human body in 2D domain and can be used for training the machine learning models. For example, the systems can use the information from the 2D joint model to obtain the 3D body shape model of the human body. The systems can also use other information, such as user's age, weight, gender, ethnic group, etc., which can be entered by the user via the user interaction and display system (e.g., 102, 302 in FIGS. 1 and 3). In some examples, a joint model can include a plurality of parameters representing skeletal joint positions. As such, training the 2D joint model includes training the parameters of the 2D joint model.

In some examples, the systems can receive captured user images (e.g., from the image capture system 104 in FIG. 1) and use the received images to estimate the body joints (in 2D domain) via a machine learning network. The systems can obtain a contour of the human body from the trained 2D joint model by connecting the joints in the 2D joint model, followed by an image dilation. The contour defines the exterior boundary of the user's 2D representation.

Returning to FIGS. 1 and 3, the systems can be configured to train user body heatmap thresholds. A user body heatmap can include a visual representation of body scan parameters. For example, a user body heatmap can include representation of body fat and/or bone mineral density of a human body.

In some examples, the body heatmap can be produced based on the body scan parameters in a body scan database. The systems can produce the heatmap and display the body scan parameters (e.g., body fat, bone mineral density) in one or more colors depending on the thresholds. In some examples, the systems can train a machine learning model to learn the heatmap thresholds and use the trained machine learning model to predict a future human body heatmap from captured user images. In some examples, the training of the heatmap thresholds can be performed on an individual basis, which allows the system to be able to monitor/estimate an individual's body parameters over time.

Examples of the machine learning models used in the systems and processes described in FIGS. 1-4 can include adapting networks such as U-net, V-net, MobileNet or other machine learning models. Additionally and/or alternatively, the machine learning model can also include a suitable convolution neural network (CNN), such as VGG or other CNNs. In some examples, the machine learning models can be learned from user images and the medical images together via co-registration of these two types of images.

Figure 5:
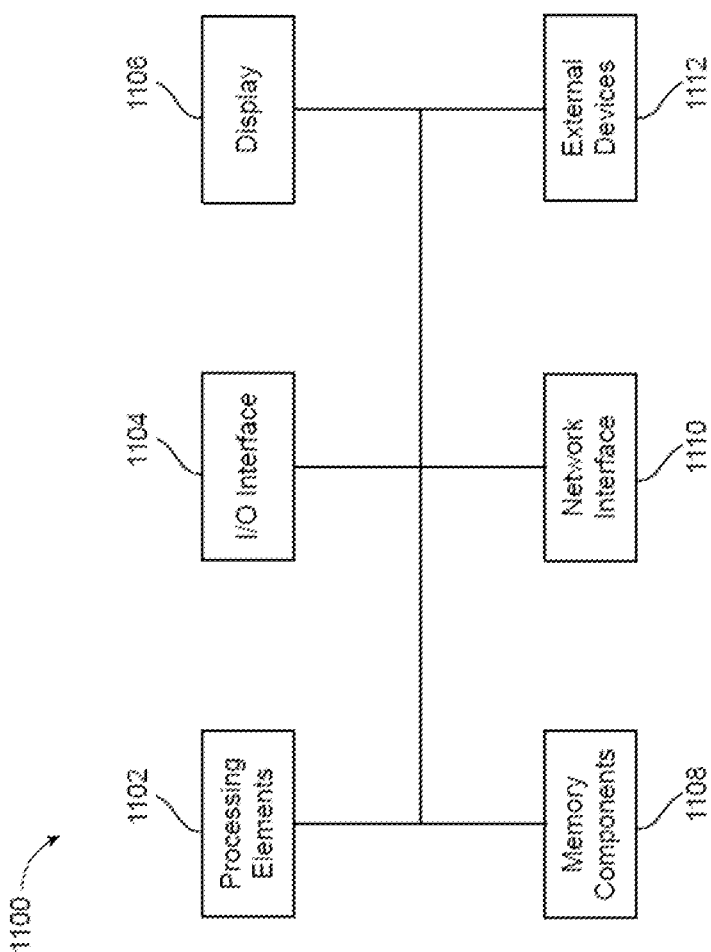
FIG. 5 is a block diagram of a computing device that can be used to implement with the various systems or integrated into one or more components of the systems according to some examples described in the disclosure.

FIG. 5 shows a simplified block structure for a computing device that can be used with the system 100 (in FIG. 1) or integrated into one or more components of the system. For example, the image capture system 104, 304, the user interaction and display system 102, 302, the biomarker extraction systems 106, 108, the feature extraction system 308, and/or other components in the systems 100, 300 (FIGS. 1 and 3) can include one or more of the components shown in FIG. 5 and be used to implement one or more blocks or execute one or more of the components or operations disclosed in FIGS. 1-4. In FIG. 5, the computing device 1100 can include one or more processing elements 1102, an input/output interface 1104, a display 1106, one or more memory components 1108, a network interface 1110, and one or more external devices 1112. Each of the various components can be in communication with one another through one or more busses, wireless means, or the like.

The processing element 1102 can be any type of electronic device capable of processing, receiving, and/or transmitting instructions. For example, the processing element 1102 can be a central processing unit, microprocessor, processor, or microcontroller. Additionally, it should be noted that some components of the computer 1100 can be controlled by a first processor and other components can be controlled by a second processor, where the first and second processors can or may not be in communication with each other.

The memory components 1108 are used by the computer 1100 to store instructions for the processing element 1102, as well as store data, such as the machine learning models and/or training images or training data, and the like. The memory components 1108 can be, for example, magneto-optical storage, read-only memory, random access memory, erasable programmable memory, flash memory, or a combination of one or more types of memory components.

The display 1106 provides audio and/or visual guidance to a user, such as displaying skeletons or other visual representations to guide the user in capturing one or more user images, or display other visual representation as can be implemented in the user interaction and display system 102, 302 (FIGS. 1 and 3). Optionally, the display 1106 can act as an input element to enable a user to control, manipulate, and calibrate various components of the computing device 1100. The display 1106 can be a liquid crystal display, plasma display, organic light-emitting diode display, and/or other suitable display. In embodiments where the display 1106 is used as an input, the display can include one or more touch or input sensors, such as capacitive touch sensors, resistive grid, or the like.

The I/O interface 1104 allows a user to enter data into the computer 1100, as well as provides an input/output for the computer 1100 to communicate with other devices or services. The I/O interface 1104 can include one or more input buttons, touch pads, and so on.

The network interface 1110 provides communication to and from the computer 1100 to other devices. For example, the network interface 1110 allows the systems 100 (FIG. 1) to communicate with various components in the system through a communication network. The network interface 1110 includes one or more communication protocols, such as, but not limited to Wi-Fi, Ethernet, Bluetooth, and so on. The network interface 1110 can also include one or more hardwired components, such as a Universal Serial Bus (USB) cable, or the like. The configuration of the network interface 1110 depends on the types of communication desired and can be modified to communicate via Wi-Fi, Bluetooth, and so on.

The external devices 1112 are one or more devices that can be used to provide various inputs to the computing device 1100, e.g., mouse, microphone, keyboard, trackpad, or the like. The external devices 1112 can be local or remote and can vary as desired. In some examples, the external devices 1112 can also include one or more additional sensors that can be used in obtaining disease risk assessment.

The foregoing description has a broad application. For example, while examples disclosed herein can focus on central communication system, it should be appreciated that the concepts disclosed herein can equally apply to other systems, such as a distributed, central or decentralized system, or a cloud system. For example, the machine learning model (e.g., 110 in FIG. 1, 310 in FIG. 3), or other components can be residing on a server in a client/server system. The machine learning model can also reside on any device, e.g., a mobile phone, on the network and operate in a decentralized manner. The machine learning model, or a portion thereof can also be residing in a controller virtual machine (VM) or a hypervisor in a VM computing environment. Accordingly, the one or more components in the system 100, 300 (FIGS. 1 and 3) can be implemented in various configurations to achieve an optimal performance in terms of accuracy and processing speed. Thus, the disclosure is meant only to provide examples of various systems and methods and is not intended to suggest that the scope of the disclosure, including the claims, is limited to these examples.

The various embodiments described in FIGS. 1-5 provide advantages in assessing a user's disease risks based on user images captured from a mobile phone or other image capture devices, without requiring any expensive equipment at prescribed locations. The training and using of various machine learning models in the assessment systems provide advantages in achieving high accuracy.

From the foregoing it will be appreciated that, although specific embodiments of the disclosure have been described herein for purposes of illustration, various modifications can be made without deviating from the spirit and scope of the disclosure. Accordingly, the scope of the disclosure should not be limited any of the specific embodiments described herein.

What is claimed is:

1. An apparatus comprising:
   an input data module configured to retrieve first input data and second input data;
   a processor; and
   a computer readable medium containing programming instructions that, when executed, will cause the processor to:
      create a 3D body shape model from the first input data and the second input data, the 3D body shape model including biometrics;
      extract biomarker data from the second input data;
      use the biometrics and biomarker data to generate health risk indicators and assessments including a first disease risk assessment value;
      generate a second risk assessment value based on the second input data; and
      fuse the biometrics with the first and second input data, and optionally the first disease risk assessment value and the second disease risk assessment value to generate a multi-category disease risk assessment value.

2. The apparatus of claim 1, wherein the input data module is integrated with an image capturing device configured to capture one or more images of a subject.

3. The apparatus of claim 2, wherein the second input data includes the one or more images of the subject.

4. The apparatus of claim 3, wherein the first disease risk assessment value is based on the one or more images.

5. The apparatus of claim 1, wherein the first disease includes diabetes.

6. The apparatus of claim 5, wherein the second disease includes cardiovascular disease.

7. An apparatus comprising:
   an image capturing device configured to capture one or more images of a subject;
   a processor; and
   computer readable medium containing programming instructions that, when executed, will cause the processor to:
      use a 3D body shape model to generate a diabetes risk assessment value based on the one or more images;
      extract biomarker data from the one or more images;
      use biomarker data to generate a cardiovascular risk assessment value based on the one or more images; and
      fuse the diabetes risk assessment value and the cardiovascular risk assessment value to generate a disease risk assessment value.

8. The apparatus of claim 7, wherein the programming instructions are further configured to update the 3D body shape model based on an output of the fusion of the diabetes risk assessment value and the cardiovascular risk assessment value.

9. The apparatus of claim 7, wherein the programming instructions are further configured to:
   use the 3D body shape model to generate first biomarkers from the one or more images, the first biomarkers representing body features; and
   generate the diabetes risk assessment value based on the body features.

10. The apparatus of claim 9, wherein the first biomarkers comprise one or more of: 3D body shapes or body shape indicators.

11. The apparatus of claim 10, wherein the diabetes risk assessment value indicates a risk associated with one or more of: type-2 diabetes, obesity, central obesity, or metabolic syndrome.

12. The apparatus of claim 7, wherein the programming instructions are further configured to:
   generate second biomarkers from the one or more images, the second biomarkers representing heart disease related biomarkers; and
   generate the cardiovascular assessment value based on the second biomarkers.

13. The apparatus of claim 12, wherein the second biomarkers comprise one or more of: blood flow, blood pressure, heart rate, respiratory rate, heart rate variability, cardiac workload, irregular heartbeats, or stress index.

14. The apparatus of claim 13, wherein the cardiovascular risk assessment value indicates a risk associated with one or more of: cardiovascular disease, heart attack, or stroke.

15. The apparatus of claim 12, wherein the programming instructions are further configured to generate the second biomarkers from facial images of the one or more images, wherein the second biomarkers comprise at least blood flow.

16. An apparatus comprising:
   an input data module configured to retrieve input data of a subject;
   a processor; and
   computer readable medium containing programming instructions that, when executed, will cause the processor to:
      use a disease risk model to generate a human body feature from the input data; and
      generate a disease risk assessment value based on the human body feature;
   wherein the human body feature comprises at least:
      one or more of: 3D body shape, or body shape indicators; and
      one or more of: blood flow, blood pressure, heart rate, respiratory rate, heart rate variability, cardiac workload, irregular heartbeats, or stress index.

17. The apparatus of claim 16, wherein the disease risk assessment value indicates a risk associated with at least:
   one or more of: type-2 diabetes, obesity, central obesity, or metabolic syndrome; and
   one or more of: cardiovascular disease, heart attack, or stroke.

18. The apparatus of claim 17, wherein the programming instructions are further configured to generate the disease risk model from one or more training images using a machine learning network.

19. The apparatus of claim 16, wherein the input data module comprises an image capture device configured to capture one or more images of the subject.

20. The apparatus of claim 19, wherein the input data comprises the one or more images of the subject.

* * * * *